(12) United States Patent
Johnson

(10) Patent No.: US 12,336,904 B2
(45) Date of Patent: Jun. 24, 2025

(54) ANCHORING FRAME DEVICE FOR AN ARTIFICIAL VALVE AND RELATED SYSTEMS AND METHOD

(71) Applicant: Johnson Consulting LLC, Chanhassen, MN (US)

(72) Inventor: Derek Johnson, Chanhassen, MN (US)

(73) Assignee: Johnson Consulting LLC, Chanhassen, MN (US)

( * ) Notice: Subject to any disclaimer, the term of this patent is extended or adjusted under 35 U.S.C. 154(b) by 133 days.

(21) Appl. No.: 17/675,441

(22) Filed: Feb. 18, 2022

(65) Prior Publication Data

US 2022/0265421 A1  Aug. 25, 2022

Related U.S. Application Data

(60) Provisional application No. 63/151,367, filed on Feb. 19, 2021.

(51) Int. Cl.
*A61F 2/24* (2006.01)

(52) U.S. Cl.
CPC .......... *A61F 2/2409* (2013.01); *A61F 2/2466* (2013.01); *A61F 2220/0016* (2013.01); *A61F 2230/0067* (2013.01)

(58) Field of Classification Search
CPC ............... A61F 2/2409; A61F 2/2466; A61F 2220/0016; A61F 2230/0067; A61F 2/2418; A61F 2/2436; A61F 2/2412
See application file for complete search history.

(56) References Cited

U.S. PATENT DOCUMENTS

| | | | |
|---|---|---|---|
| 8,876,886 B2 | 11/2014 | Kaufmann et al. | |
| 10,039,637 B2 | 8/2018 | Maimon et al. | |
| 2007/0156233 A1* | 7/2007 | Kapadia | A61F 2/2418 623/2.11 |
| 2009/0062841 A1* | 3/2009 | Amplatz | A61B 17/12159 606/200 |
| 2009/0138071 A1* | 5/2009 | Cheng | A61F 2/90 623/1.15 |

(Continued)

FOREIGN PATENT DOCUMENTS

| | | | | |
|---|---|---|---|---|
| CN | 112107392 A | * | 12/2020 | ........... A61F 2/2409 |
| CN | 112869915 A | * | 6/2021 | ........... A61F 2/2409 |
| WO | WO-2017066009 A1 | * | 4/2017 | ........... A61F 2/2409 |

OTHER PUBLICATIONS

HLT, HLT Meridian TAVR Valve System, https://hltmedical.com/meridian-valve/.

(Continued)

*Primary Examiner* — Suzette J Gherbi
(74) *Attorney, Agent, or Firm* — Fredrikson & Byron, P.A.

(57) ABSTRACT

Various deployable valve frame device embodiments that can be implanted into a valvular annulus for receiving an artificial valve therein. The frame can have an anchoring bowl, an anchoring lip, and a neck coupling the anchoring bowl to the anchoring lip, the neck comprising a lumen defined therethrough, wherein the frame is expandable from an undeployed configuration to a deployed configuration. The anchoring bowl can be convexly-shaped with an upper rim having a larger diameter than a base rim. The anchoring lip can comprise at least one prong extending radially from the anchoring lip.

21 Claims, 7 Drawing Sheets

(56) References Cited

U.S. PATENT DOCUMENTS

| | | | | |
|---|---|---|---|---|
| 2013/0304200 | A1* | 11/2013 | McLean | A61F 2/2418 |
| | | | | 623/2.18 |
| 2013/0310928 | A1* | 11/2013 | Morriss | A61F 2/2466 |
| | | | | 623/2.18 |
| 2014/0324164 | A1* | 10/2014 | Gross | A61F 2/2418 |
| | | | | 623/2.37 |
| 2015/0272737 | A1* | 10/2015 | Dale | A61F 2/2442 |
| | | | | 623/2.37 |
| 2017/0128203 | A1* | 5/2017 | Zhang | A61F 2/2436 |
| 2017/0216027 | A1* | 8/2017 | Marchand | A61F 2/2436 |
| 2017/0367822 | A1* | 12/2017 | Naor | A61F 2/2418 |
| 2018/0318071 | A1* | 11/2018 | Lozonschi | A61F 2/2412 |
| 2020/0069423 | A1* | 3/2020 | Peterson | A61F 2/9522 |

OTHER PUBLICATIONS

Hot AXIOS Stent, https://www.bostonscientific.com/en-EU/products/stents-gastrointestinal/axios-stent-and-electrocautery-enhanced-delivery-system.html.

* cited by examiner

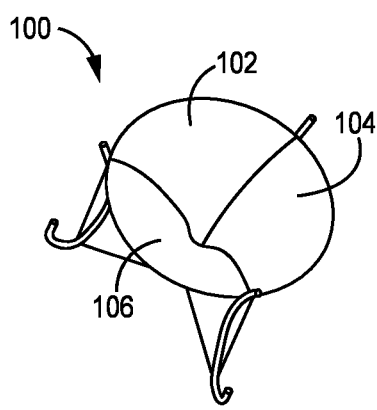 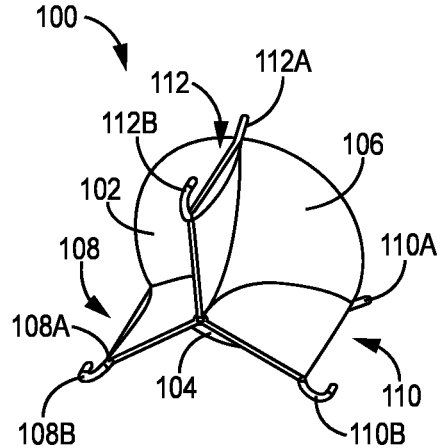
FIG. 6A    FIG. 6B
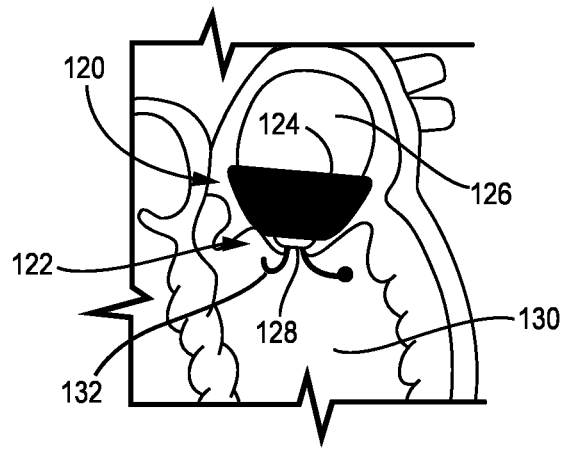
FIG. 7
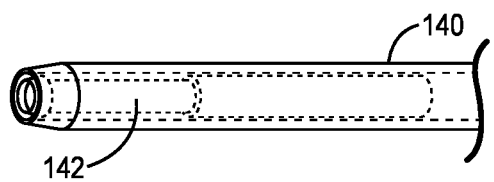
FIG. 8

ANCHORING FRAME DEVICE FOR AN ARTIFICIAL VALVE AND RELATED SYSTEMS AND METHOD

CROSS-REFERENCE TO RELATED APPLICATION(S)

This application claims the benefit under 35 U.S.C. § 119(e) to U.S. Provisional Application 63/151,367, filed Feb. 19, 2021 and entitled "Anchoring Frame Device for an Artificial Valve and Related Systems and Methods," which is hereby incorporated herein by reference in its entirety.

FIELD

The various embodiments herein relate to valvular repair and/or replacement devices and methods, including temporary frame devices for receiving temporary artificial valves.

BACKGROUND

Known valve docking stations and temporary repair implants are used to treat damaged valvular annuli in patients.

Most known devices involve either expansion or constraint of the valve annulus radially. For example, certain known designs include a ring that encircles the native leaflets and pulls them closer together, while other known devices include an implant that is embedded into the annular wall and pulls the valve inwards.

One disadvantage of the known devices is the lack of consistency and accuracy in the implantation procedure. A further disadvantage is that these known devices cannot accommodate variation in patient anatomies and thus must be provided in various sizes. Yet another disadvantage in some known devices is that they require invasive anchoring methods such as barbs, screws, or other anchors that penetrate the heart muscle or native leaflets. In addition, certain known devices are not minimally invasive and thus result in more complex procedures that require more time.

There is a need in the art for improved implantable valve prostheses and related systems and methods.

BRIEF SUMMARY

Discussed herein are various deployable valve frames that can be implanted into a valvular annulus and configured to receive an artificial valve, and related systems and methods.

In Example 1, a deployable valve frame comprises an anchoring bowl, an anchoring lip, and a neck coupling the anchoring bowl to the anchoring lip, the neck comprising a lumen defined therethrough, wherein the frame is expandable from an undeployed configuration to a deployed configuration.

Example 2 relates to the deployable valve frame according to Example 1, wherein the anchoring bowl is a convexly-shaped anchoring bowl comprising an upper rim and a base rim, wherein the upper rim has a larger diameter than the base rim.

Example 3 relates to the deployable valve frame according to Example 2, wherein the neck is coupled to the base rim via a collar.

Example 4 relates to the deployable valve frame according to Example 1, wherein the lumen is configured to receive an implantable artificial valve.

Example 5 relates to the deployable valve frame according to Example 1, wherein the anchoring bowl is a concavely-shaped anchoring bowl comprising a bowl wall extending from a proximal end of the neck to an outer rim.

Example 6 relates to the deployable valve frame according to Example 1, wherein the anchoring lip comprises at least one prong extending radially from the anchoring lip.

Example 7 relates to the deployable valve frame according to Example 1, wherein the anchoring lip comprises at least two prongs extending radially from the anchoring lip, wherein the at least two prongs are spaced symmetrically around a circumference of the lip in relation to each other.

Example 8 relates to the deployable valve frame according to Example 1, wherein the anchoring lip comprises three prongs extending radially from the anchoring lip, wherein each of the three prongs is disposed about 120 degrees around the circumference of the lip from the other two of the three prongs.

In Example 9, a deployable valve frame comprises a bowl-shaped anchor, wherein the anchor is convexly shaped or concavely shaped, a lip anchor, and a neck coupling the bowl-shaped anchor to the lip anchor, the neck comprising a lumen defined therethrough, wherein the lumen is configured to receive an implantable artificial valve, wherein the frame is expandable from an undeployed configuration to a deployed configuration.

Example 10 relates to the deployable valve frame according to Example 9. further comprising an implantable artificial valve positionable within the lumen.

Example 11 relates to the deployable valve frame according to Example 9, wherein the neck is configured to fit within a native mitral annulus.

Example 12 relates to the deployable valve frame according to Example 11, wherein the neck comprises an elliptical-shaped outer diameter, whereby the neck is configured to conform with a shape of the native mitral annulus.

Example 13 relates to the deployable valve frame according to Example 9. wherein the lip anchor comprises at least one prong extending radially from the lip anchor.

Example 14 relates to the deployable valve frame according to Example 9. wherein the lip anchor comprises at least two prongs extending radially from the lip anchor, wherein the at least two prongs are spaced symmetrically around a circumference of the lip anchor in relation to each other.

Example 15 relates to the deployable valve frame according to Example 9. wherein the lip anchor comprises three prongs extending radially from the lip anchor, wherein each of the three prongs is disposed about 120 degrees around the circumference of the lip anchor from the other two of the three prongs.

In Example 16, a deployable valve frame comprises an anchoring bowl comprising a concave shape, an anchoring lip comprising at least two prongs extending radially from the anchoring lip, and a neck coupling the anchoring bowl to the anchoring lip. The anchoring bowl extends from a proximal end of the neck and the anchoring lip extends from a distal end of the neck, wherein the neck comprises a lumen defined therethrough, and wherein the lumen is sized and shaped to receive an implantable artificial valve. And the frame is expandable from an undeployed configuration to a deployed configuration.

Example 17 relates to the deployable valve frame according to Example 16, wherein the anchoring bowl comprises a bowl wall extending radially and distally from the proximal end of the neck to an outer rim.

Example 18 relates to the deployable valve frame according to Example 17, wherein the outer rim has a diameter ranging from about 28 mm to about 42 mm.

Example 19 relates to the deployable valve frame according to Example 16, wherein the anchoring bowl further comprises a bowl lip extending radially from the outer rim.

Example 20 relates to the deployable valve frame according to Example 16, wherein the anchoring lip has a width ranging from about 1 mm to about 5 mm, wherein each of the at least two prongs extends radially from the neck a distance ranging from about 5 mm to about 15 mm.

Example 21 relates to the deployable valve frame according to Example 10, wherein the implantable artificial valve comprises at least one attachment structure attached to the implantable artificial valve, wherein the at least one attachment structure comprises a rod disposed axially in relation to the implantable artificial valve and a hook disposed at a proximal end of the rod.

Example 22 relates to the deployable valve frame according to Example 10, wherein the implantable artificial valve is a temporary bi-leaflet valve comprising at least two sheets.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

BRIEF DESCRIPTION OF THE DRAWINGS

FIG. 6A is a perspective view of an artificial valve, according to another embodiment.

FIG. 6B is another perspective view of the artificial valve of FIG. 6A, according to one embodiment.

FIG. 7 is a cross-sectional side view of an implantable, expandable valve frame positioned in a mitral annulus of a patient, according to one embodiment.

FIG. 8 is a perspective view of an implantable, expandable valve frame disposed within a delivery catheter, according to one embodiment.

DETAILED DESCRIPTION

Various embodiments herein relate to an implantable valve prosthesis (or "frame") that can be positioned or implanted in a damaged valvular annulus in a patient to provide a structure or base for receiving or anchoring a subsequent artificial valve assembly. Additional implementations relate to such an implantable frame in combination with an artificial valve assembly disposed therein. Either or both of the valve frame and the valve assembly can be implanted surgically or via a minimally invasive procedure (such as transcatheter delivery, for example). In certain embodiments, the valve frame and/or valve assembly are intended for a damaged/defective mitral valve. Alternatively, the various implementations herein can be used to repair other types of cardiovascular valves in a patient, including, for example, the tricuspid valve and any other native heart valve.

According to various implementations, the various frame embodiments disclosed or contemplated herein can be implanted into a damaged/defective mitral valve with a valve assembly coupled thereto to reduce or eliminate blood leakage (regurgitation) from the left ventricle into the left atrium during the cardiac cycle. Additionally, certain device embodiments could be implanted into a damaged/defective valve to provide an improved leaflet opening area (thereby addressing an opening insufficiency). The objective, in certain embodiments, is to deliver one or both of the prosthesis and valve assembly through the vasculature via a transcatheter technique and permanently implant them into the existing mitral annulus.

Figure 1A:
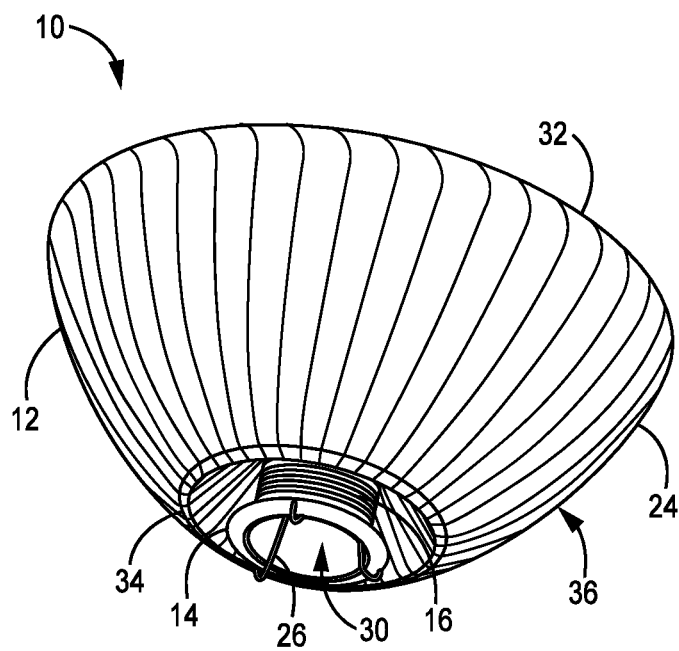
FIG. 1A is a perspective view of an implantable, expandable valve frame, according to one embodiment.
Figure 1B:
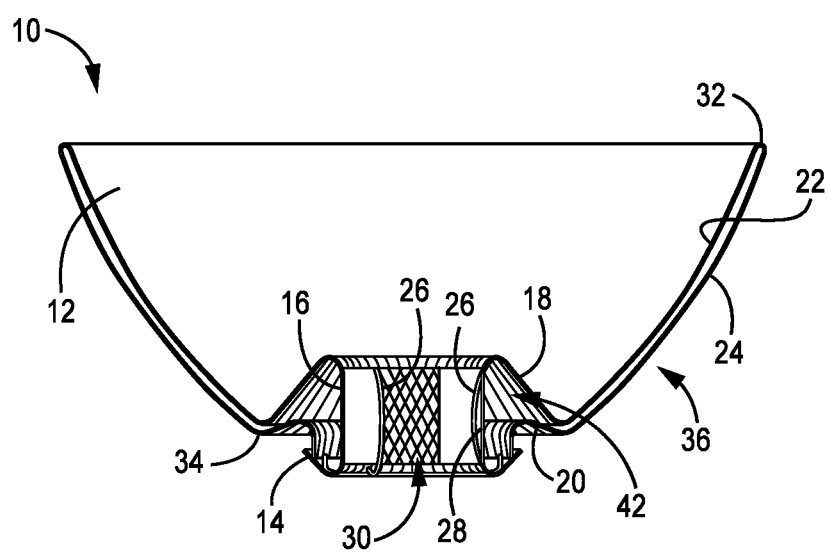
FIG. 1B is a cross-sectional side view of the implantable, expandable valve frame of FIG. 1A, according to one embodiment.
Figure 1C:
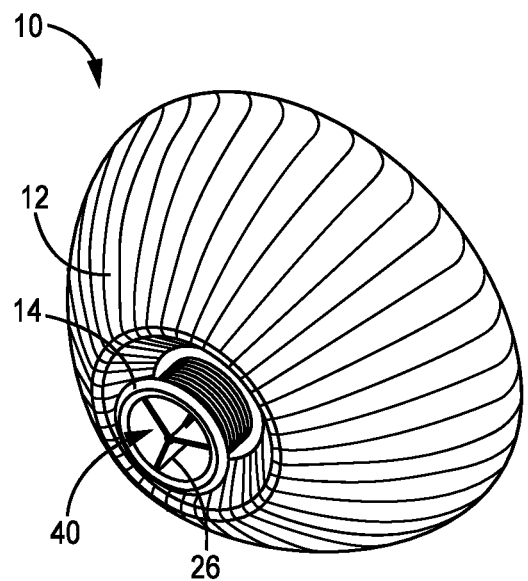
FIG. 1C is another perspective view of the implantable, expandable valve frame of FIG. 1A, according to one embodiment.

One exemplary embodiment of an implantable, expandable valve frame 10 is depicted in FIGS. 1A-1C. The frame 10 has two anchoring components 12, 14 and a neck 16 that extends between and couples the two anchoring components 12, 14 together. The first anchoring component (also referred to as a "first anchor") 12 is an expandable, convexly-shaped anchor or "bowl" 12 that is configured to be positioned within a first cavity of a patient and expand to anchor the frame 10 in place as a result of the positioning of the anchor 12 such that a wall 36 of the anchor 12 expands into contact with an inner wall of the first cavity. More specifically, in certain implementations, the first anchor 12 is disposed within the atrium—such as the left atrium—of a patient such that the expandable bowl shape of the first anchor 12 results in the wall 36 being in contact with the inner surface of the atrium. The anchoring of the anchor 12 in the atrium (such as, for example, the left atrium) is accomplished via a compression or friction coupling between the wall 36 of the anchor 12 and the inner surface of the atrium when the anchor 12 expands.

The second anchoring component (also referred to as a "second anchor") 14 is a curved lip (or "protrusion") 14 that extends from one end of the neck 16. The second anchor 14 is configured to be positioned within a second cavity of the patient and anchor the frame 10 in place as a result of the positioning of the anchor 14 such that the lip 14 is positioned in contact with an inner wall of the second cavity. More specifically, in certain implementations, the second anchor 14 is disposed within the ventricle (such as the left ventricle) of the patient such that the curved lip configuration results in the lip 14 being in contact with the inner surface of the ventricle. The anchoring of the anchor 14 in the ventricle is accomplished via a compression or friction coupling between lip 14 and the inner surface of the ventricle.

As discussed in additional detail below, the positioning of the first anchor 12 within the first cavity (such as the left atrium, for example) and the second anchor 14 in the second cavity (such as the left ventricle, for example) results in the neck 16 being disposed within the annulus of the target valve. As such, the two anchors 12, 14 are configured to properly position the neck 16 and thus the entire frame 10 within the target annulus such that the frame 10 is anchored in the annulus and can be used to retain an artificial valve therein.

According to certain implementations, the neck 16 has a lumen 30 that receives an implanted replacement valve. The lumen 30 can have a consistent inner diameter across multiple devices to enable the same size replacement valve to be utilized. Alternatively, different devices can have a neck 16 with a variety of predetermined diameters to accommodate variation in annulus dimensions, including, for example, mitral annulus dimensions. According to certain implementations, the neck 16 can be expandable in a fashion similar to the first anchor 12 such that the neck 16 can anchor to the annular wall via radial expansion of the neck 16 into contact with the annular wall. According to certain embodiments, the neck 16 has an inner diameter ranging from about 24 mm to about 32 mm. Alternatively, the neck 16 has an inner diameter ranging from about 25 mm to about 30 mm. In a further embodiment, the neck 16 has an inner diameter ranging from about 26 mm to about 29 mm. Specific inner diameters can include, but are not limited to, about 25, 26, 27, 28, 29, and 30 mm. In accordance with some embodiments, the neck 16 has an outer diameter ranging from about 23 mm to about 40 mm. Alternatively, the neck 16 has an elliptical shape with a minor outer diameter between about 28 mm to about 34 mm and a major outer diameter between about 34 mm and about 40 mm.

In certain embodiments, the first, bowl-shaped anchoring component 12 has an outer (or "upper") rim 32 and a base rim 34, with the wall 36 extending from the base rim 34 to the outer rim 32. According to certain embodiments, the outer rim 32 has a diameter ranging from about 40 mm to about 55 mm. Alternatively, the outer rim 32 has a diameter ranging from about 43 mm to about 52 mm. In a further alternative, the outer rim 32 has a diameter ranging from about 45 mm to about 50 mm. According to certain embodiments, the base rim 34 has a diameter ranging from about 28 mm to about 42 mm. Alternatively, the base rim 34 has a diameter ranging from about 30 mm to about 40 mm. In a further alternative, the base rim 34 has a diameter ranging from about 33 mm to about 38 mm. The linear height of the wall 36—the length of the wall 36 between the base rim 34 and the outer rim 32—can range from about 0 mm to about 16 mm Alternatively, the linear height of the wall 36 can range from about 2 mm to about 12 mm. In a further alternative, the linear height of the wall 36 can range from about 4 mm to about 8 mm. In addition, according to one alternative embodiment, the linear height can be about 5 mm.

According to certain embodiments, the outer diameter of the lip 14 has a diameter ranging from about 35 mm to about 50 mm. Alternatively, the outer diameter of the lip 14 ranges from about 37 mm to about 47 mm. In a further alternative, the outer diameter of the lip 14 ranges from about 40 mm to about 45 mm. Further, according to certain embodiments, the width of the lip 14 (the distance that the lip 14 extends radially from the outer surface of the neck 16) ranges from about 0 mm to about 15 mm. Alternatively, the width of the lip 14 ranges from about 5 mm to about 15 mm. In a further alternative, the width of the lip 14 extends a distance from the outer surface of the neck 16 that ranges from about 8 mm to about 12 mm. In addition, according to certain implementations, the outer edge of the lip 14 extends a distance proximally from the end of the neck 16 that ranges from about 0 mm to about 15 mm. Alternatively, the outer edge of the lip 14 extends a distance from the end of the neck 16 that ranges from about 2 mm to about 10 mm. In a further alternative, the outer edge of the lip 14 extends a distance from the end of the neck 16 that ranges from about 5 mm to about 8 mm.

According to one embodiment, as best shown in FIG. 1B, the anchor 12 is coupled to the neck 16 via a collar 18, which extends radially from the proximal end of the neck 16 at an angle as shown. The collar 18 is coupled to or integral with the anchor 12 at the base rim 34. As such, the outer wall of the neck 16 and the collar 18 create a recess 42 therebetween. In certain embodiments, the device 10 has a flap or cover 20 that extends across the recess 42 from the anchor 12 to the anchor 14 to cover and block fluidic access to the recess 42. In other words, the flap 20 prevents fluidic access to the recess 42 such that it prevents stagnant blood flow or blood pooling within the recess and thereby prevents thrombus formation. In one embodiment, the flap 20 is a part of the braided shape memory material of the device 10. Alternatively, as will be discussed in further detail below, the flap 20 can be part of a cover that is disposed over the device 10.

According to certain alternative implementations, the frame 10 can have attachment structures 26 disposed within the neck 16 that can be used to attach an artificial valve thereto. More specifically, that attachment structures 26 are attachment rods or wires 26, each having curved hooks 28 disposed at the distal end of each rod 26 such that the curved hooks 28 can be positioned at the distal end of the neck 16 as best shown in FIGS. 1A and 1B. In a specific example, an exemplary artificial valve 40, as shown in FIG. 1C, is disposed within the lumen 30 and attached to three attachment structures 26 as will be described in additional detail below. As such, in certain embodiments such as that shown in FIG. 1C, the frame 10 can have such a valve 40 attached thereto such that the frame 10 and valve 40 make up a full, pre-assembled valve replacement assembly. Alternatively, the frame 10 can have any known structures or features for assisting with attachment of an artificial valve within the lumen 30 of the neck 16. According to various implementations, the attachment structures can work in conjunction with the second anchor 14 to assist with anchoring to the inner wall of the second cavity (or ventricle).

In certain implementations, the entire frame 10 is made of a woven or braided strand or two or more such strands that can be made of the same material or different materials and is expandable and compressible as described herein. Exemplary materials include any known shape memory alloy, such as, for example, Nickel Titanium ("Nitinol"). According to some embodiments, the material is a braided shape memory material (such as, for example, a shape memory alloy) that allows for any frame embodiment disclosed or contemplated herein to undergo significant diameter reduction to allow for vascular delivery in a catheter and expansion during implantation to provide for proper fit within the target annulus. More specifically, the woven braid frame and shape memory material will allow for large radial deformations to enable a smaller profile during sheathing and large expansion during deployment to anchor in the target area of the patient. As such, the woven frame and shape memory material can enhance the effectiveness of the two anchoring members, such that the woven frame shape memory material enhance the frictional coupling of the first anchor with the inner surface of the first cavity and further enhance the frictional coupling of the second anchor with the inner surface of the second cavity.

Alternatively, the frame 10 can be an expandable/compressible stent structure that is made using a machined device construction method. In a further alternative, the device can be made of any known structure or method that results in an expandable and compressive frame.

As best shown in FIG. 1B, the frame 10 can also have a cover material disposed over the internal braided material of the first anchor 12. More specifically, in this specific exemplary embodiment, the cover material is a fabric material having an inner sheet 22 and an external sheet 24 that fully cover the inner and outer surfaces of the wall 36. Alternatively, the cover material can be disposed around every component of the frame 10. The cover material can be woven, spun, or wrapped sheets of any known polymer, such as, for example, polyester. Alternatively, the cover material can be any known material that can be woven, spun, or wrapped for use in covering an implant as described herein. The cover 22, 24 can help to promote tissue growth/healing and improve the sealing properties of the device 10. In certain implementations, the external sheet 24 can also include the flap 20 discussed above that covers the recess 42 and prevents blood pooling therein.

Figure 2:
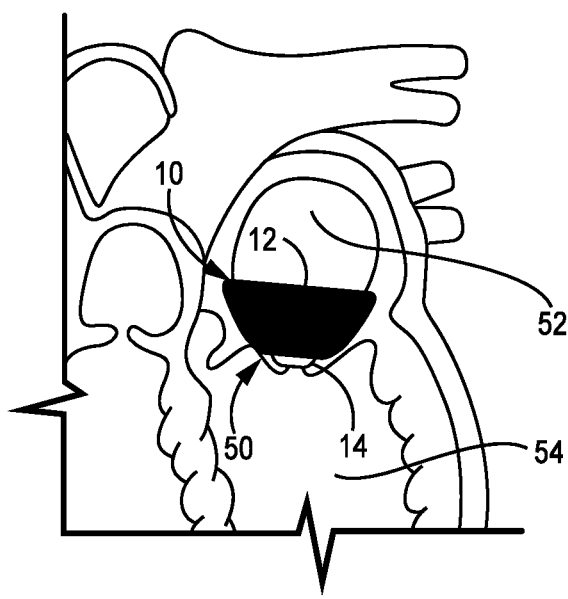
FIG. 2 is a cross-sectional side view of an implantable, expandable valve frame positioned in a mitral annulus of a patient, according to one embodiment.

In use, as shown in FIG. 2, the device 10 can be positioned in the mitral annulus 50 such that the first anchor 12 is disposed within the left atrium 52 and the second anchor 14 is disposed within the left ventricle 54. As discussed above, the first anchor 12 as shown has expanded into frictional contact with the inner walls of the left atrium 52.

Figure 3A:
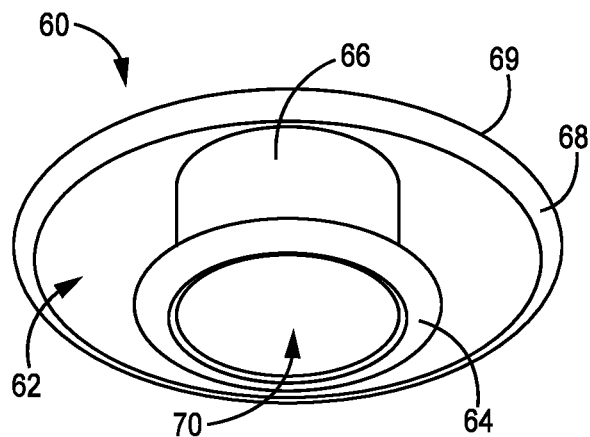
FIG. 3A is a perspective view of another implantable, expandable valve frame, according to a further embodiment.
Figure 3B:
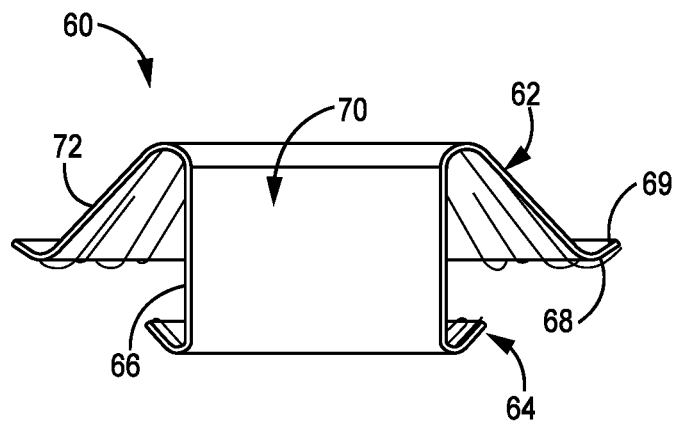
FIG. 3B is a cross-sectional side view of the implantable, expandable valve frame of FIG. 3A, according to one embodiment.
Figure 3C:
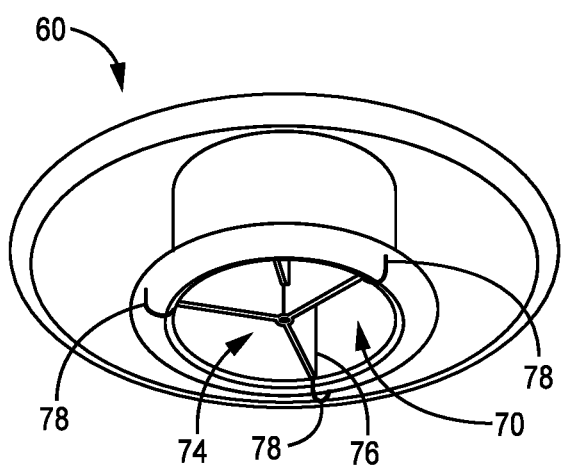
FIG. 3C is another perspective view of the implantable, expandable valve frame of FIG. 3A with an artificial valve disposed therein, according to one embodiment.

An alternative implantable, expandable valve frame 60 is depicted in FIGS. 3A-3C. Like the device 10, the device 60 has two anchoring components 62, 64 and a neck 66 that extends between and couples the two anchoring components 62, 64 together. In this embodiment, the first anchoring component 62 is an expandable, concavely-shaped anchor or "bowl" 62 (in contrast to the convexly-shaped bowl 12 of the device 10 as described in detail above) that is configured to be positioned within a first cavity of a patient and expand to anchor the frame 60 in place as a result of the positioning of the anchor 62 such that an outer rim 68 of the bowl 62 is disposed in contact with an inner wall of the first cavity. More specifically, in certain implementations, the first anchor 62 is disposed within the atrium—such as the left atrium—of a patient such that the expandable bowl shape of the first anchor 62 results in the outer rim 68 being in contact with the inner surface of the atrium. The anchoring of the anchor 62 in the atrium (such as, for example, the left atrium) is accomplished via a compression or friction coupling between the wall outer rim 68 of the anchor 62 and the inner surface of the atrium when the anchor 62 is positioned correctly.

The second anchoring component (also referred to as a "second anchor") 64 is substantially similar to the second anchor 14 of the device 10 discussed in detail above. That is, the second anchor 64 is a curved lip (or "protrusion") 64 that extends from the distal end of the neck 66. The second anchor 64 is configured to be positioned within a second cavity of the patient and anchor the frame 60 in place as a result of the positioning of the anchor 64 such that the lip 64 is positioned in contact with an inner wall of the second cavity. More specifically, in certain implementations, the second anchor 64 is disposed within the ventricle (such as the left ventricle) of the patient such that the curved lip configuration results in the lip 64 being in contact with the inner surface of the ventricle. The anchoring of the anchor 64 in the ventricle is accomplished via a compression or friction coupling between lip 64 and the inner surface of the ventricle.

Except where specifically discussed herein, the various additional components, features, and functions of the device 60 are substantially similar to those of the device 10 discussed above. Thus, the positioning of the first anchor 62 within the first cavity and the second anchor 64 in the second cavity results in the neck 66 being disposed within the annulus of the target valve. As such, the two anchors 62, 64 are configured to properly position the neck 66 and thus the entire frame 60 within the target annulus such that the frame 60 is anchored in the annulus and can be used to retain an artificial valve therein. Further, the neck 66 has a lumen 70 that receives an implanted replacement valve.

In certain embodiments, the concave anchoring component 62 has a wall 72 that extends from the proximal end of the neck 66 to the outer rim 68. The size of the wall 72—the length of the wall 72 between the neck 66 and the outer rim 68 can range from about 5 mm to about 15 mm. Alternatively, the length of the wall 72 can range from about 7 mm to about 12 mm. According to certain embodiments, the outer rim 68 has a diameter ranging from about 28 mm to about 42 mm. Alternatively, the outer rim 68 has a diameter ranging from about 30 mm to about 40 mm. In a further alternative, the outer rim 68 has a diameter ranging from about 33 mm to about 38 mm.

Further, the anchoring component 62 can also have a lip 69 extending from the outer rim 68. The lip 69 can help to minimize or eliminate tissue damage from contact with the outer rim 68. In one embodiment, the lip 69 has a width of from about 1 to about 5 mm.

In this specific implementation, the concave shape of the anchor 62 helps to minimize the number of recesses and other stagnant flow areas formed in the first cavity as a result of the device 10.

In accordance with certain embodiments, an exemplary artificial valve 74, as shown in FIG. 3C, is disposed within the lumen 70. And like the device 10 implementation discussed above, certain attachment structures 76 can be disposed within the neck 66 and used to attach an artificial valve (such as valve 74) thereto. The structures 76 can be the same structures 76 as discussed above. More specifically, attachment structures 76 are attachment rods or wires 76, each having curved hooks 78 disposed at the distal end of each rod 76 such that the curved hooks 78 can be positioned at the distal end of the neck 66 as best shown in FIGS. 3A and 3B. Alternatively, any known attachment structures can be used. Thus, in certain embodiments such as that shown in FIG. 3C, the frame 60 can have such a valve 74 attached thereto such that the frame 60 and valve 74 make up a full, pre-assembled valve replacement assembly.

Figure 4:
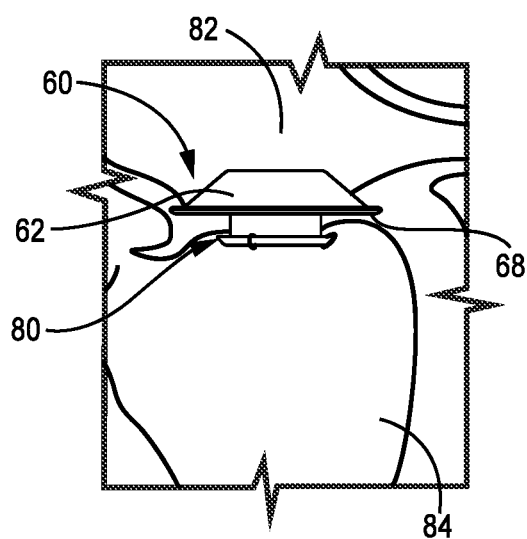
FIG. 4 is a cross-sectional side view of an implantable, expandable valve frame positioned in a mitral annulus of a patient, according to one embodiment.
Figure 5:
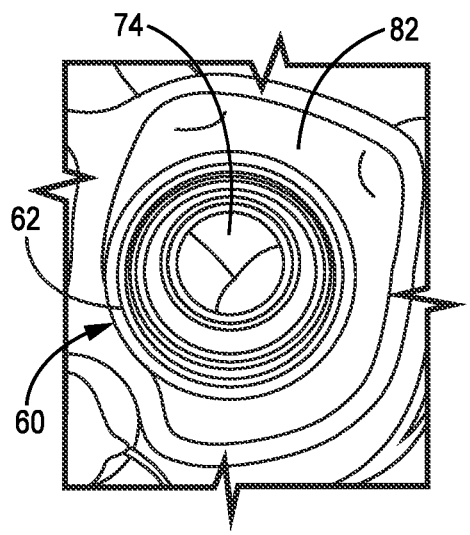
FIG. 5 is a cross-sectional perspective view of the implantable, expandable valve frame of FIG. 4 positioned in the mitral annulus, according to one embodiment.
Figure 9A:
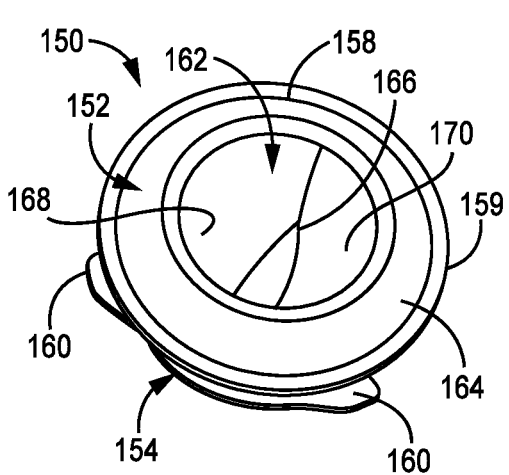
FIG. 9A is a perspective top view of another implantable, expandable valve frame, according to a further embodiment.
Figure 9B:
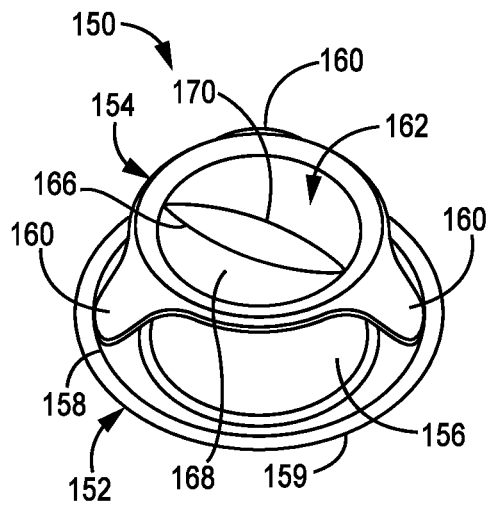
FIG. 9B is a perspective bottom view of the implantable, expandable valve frame of FIG. 9A, according to one embodiment.
Figure 9C:
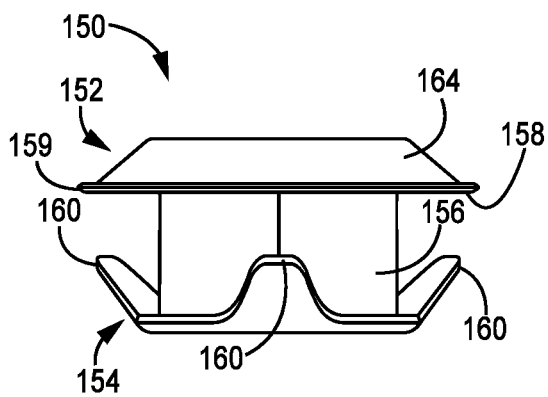
FIG. 9C is a side view of the implantable, expandable valve frame of FIG. 9A, according to one embodiment.
Figure 9D:
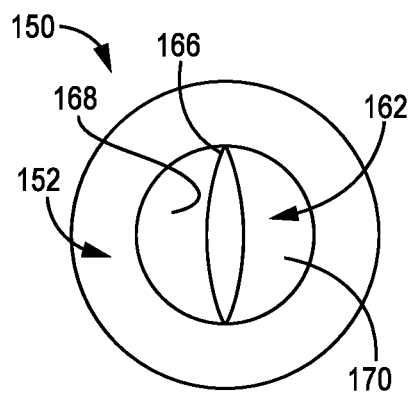
FIG. 9D is a top view of the implantable, expandable valve frame of FIG. 9A, according to one embodiment.
Figure 9E:
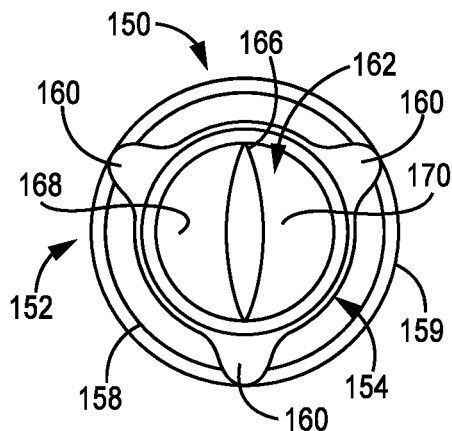
FIG. 9E is a bottom view of the implantable, expandable valve frame of FIG. 9A, according to one embodiment.

In use, as shown in FIGS. 4 and 5, the device 60 can be positioned in the mitral annulus 80 such that the first anchor 62 is disposed within the left atrium 82 and the second anchor 64 is disposed within the left ventricle 84. As discussed above, the first anchor 62 as shown is positioned such that the outer rim 68 contact with the inner walls of the left atrium 82. FIG. 4 is a cross-sectional view of the device 60 within the mitral annulus, while FIG. 5 is a top view of the device 60 with the first anchor 62 disposed within the left atrium 82 and the valve 74 disposed therein.

One specific embodiment of an artificial valve 100 that can be used with any of the frame implementations disclosed or contemplated herein is depicted in FIGS. 6A and 6B. The valve 100 has three leaflets 102, 104, 106. In this embodiment, the valve 100 is attachable to any of the frame implementations herein via the attachment devices ("commissures") 108, 110, 112. Each attachment device 108, 110, 112 has an elongate rod 108A, 110A, 112A and a distal hook 108B, 110B, 112B at a distal end of each of the rods 108A, 110A, 112A. In the specific implementation as shown, each attachment rod 108A, 110A, 112A is attached to the valve 100 at the attachment points of the leaflets 102, 104, 106 to each other. More specifically, attachment rod 108A is attached at the attachment point of leaflets 102 and 104, attachment rod 110A is attached at the attachment point of leaflets 104 and 106, and attachment rod 112A is attached to the attachment point of leaflets 106 and 102. According to the specific embodiment as shown, the three leaflets 102, 104, 106 are shaped to form a tricuspid valve 100 that allows for opening during forward flow and closing/sealing during back flow.

In use, as shown in FIG. 7, a frame 120 embodiment is positioned in the mitral annulus 122 such that the first anchor 124 is disposed within the left atrium 126 and the second anchor 128 is disposed within the left ventricle 130. Further, the anchor hooks 132 of the attachment devices are shown extending from the frame 120.

Any of the various frame (and combination frame and valve) embodiments disclosed or contemplated herein can be delivered via a minimally invasive procedure. That is, any of the various implementations herein can be expandable from a constrained, retracted configuration into an expanded or deployed configuration in which the various components discussed above are expanded to full size. Thus, the various devices herein can be delivered via a catheter to the target annulus and then deployed.

One exemplary catheter 140 is shown in FIG. 8 with a deployable frame 142 disposed therein as shown. The frame 142 is radially constrained—sheathed—within the catheter 140 to facilitate transfemoral delivery to the native, target annulus. After delivery to the implant site, the frame 142 is deployed—unsheathed—from the catheter assembly and placed into the target annulus. As described above with the various embodiments, the expanded frame is used to seal around the valve to prevent leakage and to provide anchoring. Further, in those embodiments in which the target annulus is the mitral annuls, the replacement valve assembly is used to provide a means for allowing blood flow between the atrium and the ventricle during ventricular diastole and to provide sealing during ventricular systole.

A further exemplary implementation of an implantable, expandable valve frame 150 is depicted in FIGS. 9A-9E. The frame 150 has two anchoring components 152, 154 and a neck 156 that extends between and couples the two anchoring components 152, 154 together. The first anchoring component (also referred to as a "first anchor") 152 is an expandable, concavely-shaped anchor or "bowl" 152 that is configured to be positioned within a first cavity of a patient and expand to anchor the frame 10 in place as a result of the positioning of the anchor 152 such that an outer rim 158 of the bowl 152 is disposed in contact with an inner wall of the first cavity. More specifically, in certain implementations, the first anchor 152 is disposed within the atrium—such as the left atrium—of a patient such that the expandable bowl shape of the first anchor 152 results in the outer rim 158 being in contact with the inner surface of the atrium. The anchoring of the anchor 152 in the atrium (such as, for example, the left atrium) is accomplished via a compression or friction coupling between the wall outer rim 158 of the anchor 152 and the inner surface of the atrium when the anchor 152 is positioned correctly.

The second anchoring component (also referred to as a "second anchor") 154 is a curved lip (or "protrusion") 154 that extends from one end of the neck 156 (opposite the first anchor 152) and extends from the neck around the entire circumference thereof. Further, in certain embodiments, the lip 154 has three prongs 160 extending outward from the lip 154 as shown. Alternatively, the lip 154 can have one, two, four, or any number of prongs 160. The second anchor 154 is configured to be positioned within a second cavity of the patient and anchor the frame 150 in place as a result of the positioning of the anchor 154 such that the lip 154 and the prongs 160 are positioned in contact with an inner wall of the second cavity. More specifically, in certain implementations, the second anchor 154 is disposed within the ventricle (such as the left ventricle) of the patient such that the curved lip and prong configuration results in the lip 154 and prongs 160 being in contact with the inner surface of the ventricle. The anchoring of the anchor 154 in the ventricle is accomplished via a compression or friction coupling between lip 154 and prongs 160 and the inner surface of the ventricle.

Except where specifically discussed herein, the various additional components, features, and functions of the device 150 are substantially similar to those of the device 10 and/or device 60 as discussed above. Thus, as discussed in additional detail above in relation to previous embodiments, the positioning of the first anchor 152 within the first cavity (such as the left atrium, for example) and the second anchor 154 in the second cavity (such as the left ventricle, for example) results in the neck 156 being disposed within the annulus of the target valve. As such, the two anchors 152, 154 are configured to properly position the neck 156 and thus the entire frame 150 within the target annulus such that the frame 150 is anchored in the annulus and can be used to retain an artificial valve therein.

In certain embodiments, the first, concave anchoring component 152 has a wall 164 that extends from the proximal end of the neck 156 to the outer rim 158. The size of the wall 164—the length of the wall 164 between the neck 66 and the outer rim 158 can range from about 5 mm to about 15 mm. Alternatively, the length of the wall 164 can range from about 7 mm to about 12 mm. According to certain embodiments, the outer rim 158 has a diameter ranging from about 28 mm to about 42 mm. Alternatively, the outer rim 158 has a diameter ranging from about 30 mm to about 40 mm. In a further alternative, the outer rim 158 has a diameter ranging from about 33 mm to about 38 mm.

Further, the anchoring component 152 can also have a lip 159 extending from the outer rim 158. The lip 159 can help to minimize or eliminate tissue damage from contact with the outer rim 158. In one embodiment, the lip 159 has a width of from about 1 to about 5 mm.

In certain embodiments, the concave shape of the anchor 152 helps to minimize the number of recesses and other stagnant flow areas formed in the first cavity as a result of the device 150.

In accordance with some implementations, the width of the lip 154 (the distance that the lip 154 extends radially from the outer surface of the neck 156) ranges from about 0 mm to about 5 mm. Alternatively, the width of the lip 154 ranges from about 1 mm to about 4 mm.

According to certain implementations, the prongs 160 are structures that extend farther out from the neck 156 at different radial points of the lip 154 to provide further anchoring in less traumatic ventricular areas (such as, for example, the atrial-ventricular groove or trigones). These prongs (also referred to herein as "lobes") 160 can extend, in some embodiments, an additional distance radially of about 5 to about 15 mm from the neck 156. Alternatively, the prongs 160 can extend an additional distance of about 7 to about 13 mm or, in a further alternative, about 8 to about 12 mm. The prongs 160, in some embodiments, can also extend longitudinally (parallel to a longitudinal axis of the neck 146) a distance from the distal end of the neck 146 proximally toward the annulus ranging from about 5 to about 15 mm. Alternatively, the prongs 160 can extend longitudinally and proximally from about 7 to about 13 mm or, in a further alternative, from about 8 to about 12 mm. The prongs 160 can be located symmetrically around the circumference of the lip 154 at about 120 degree intervals or alternatively may be more staggered to align with the optimal location with the ventricular apparatus.

As with the implementations discussed above, the neck 156 has a lumen 162 that is sized and configured to receive an implanted replacement valve. The lumen 162 can have the same sizes, characteristics, and features as the lumen embodiments discussed above. Further, in certain implementations, the lumen 162 can have a temporary bi-leaflet valve 166 disposed within the lumen 162 that is made up of at least one sheet of flexible material 168, 170 as shown. In this specific exemplary embodiment, the valve 166 has two sheets 168, 170. Alternatively, the valve 166 can have one sheet, three sheets, or any number of sheets. The sheets (such as sheets 168, 170) can be made up of polymeric fabric (such as, for example, PET, PTFE, or other such materials), one or more materials of animal origin (such as, for example, bovine or porcine pericardial patches), or any other known flexible material for use in such medical devices that is attached to the inner wall of the lumen 162. In certain alternative embodiments, the sheets (such as the two sheets 168, 170) can have a coating that includes an active pharmaceutical ingredient to promote or prevent tissue growth. In a further alternative, any portion of the device embodiments herein can have such a coating. The bi-leaflet valve 166 can provide temporary valvular action (opening and closing) to provide hemodynamic stability (i.e. prevent open mitral valve leakage) during the transition time period between the implantation of the frame 150 and the placement of the replacement valve within the frame 150.

In use, like the previous embodiments as described in detail above, the device 150 can be positioned in a valvular annulus 50 such that the first anchor 152 is disposed on one side of the annulus and the second anchor 154 is disposed on the other.

The various frame embodiments herein can be used to provide temporary but complete valve function during the time between implantation and subsequent transcatheter valve implantation. They enable a traditional axial displacement deployment, which differs from the radial deployment utilized by most known devices. Thus, in contrast to the radially deploying prior art devices, the direct axial deployment capabilities of the various implementations herein provide a more consistent and accurate implantation procedure and accommodate the wide variety of patient anatomies and etiologies by providing consistent anchoring locations in the atrium base structure and ventricular commissures and/or AV groove. The atrial geometry in the various device embodiments both minimizes paravalvular leakage and raises the neo valve annulus higher into the atrium, which will reduce the likelihood of ventricular obstructions (e.g. left ventricular outflow tract obstruction). Further, the various implementations herein allow for solid anchoring in the valvular annulus without requiring invasive anchoring methods used in known devices as described above. In the embodiments herein, the devices have a braided design that allows for a lower profile in the undeployed or sheathed (catheter delivery) state (in comparison to the prior art, which will reduce the procedural complexity, procedural time, and patient inclusion criteria.

Although the various embodiments have been described with reference to preferred implementations, persons skilled in the art will recognize that changes may be made in form and detail without departing from the spirit and scope thereof.

What is claimed is:

1. A deployable valve frame comprising:
   (a) a neck comprising:
      (i) a cylindrical neck body comprising an outer neck surface, an inner neck surface, a distal opening at a distal end, and a proximal opening at a proximal end; and
      (ii) a lumen defined through the cylindrical neck body by the inner neck surface, wherein the lumen is in fluidic communication with the distal opening and the proximal opening, wherein the lumen is sized and shaped to receive an implantable artificial valve;
   (b) an anchoring lip comprising:
      (i) a lip wall disposed around a circumference of the cylindrical neck body, the lip wall comprising:
         (A) a lip wall inner rim disposed at the distal end of the cylindrical neck body; and
         (B) a lip wall outer rim disposed radially external to the circumference of the cylindrical neck body and proximal of the distal end of the cylindrical neck body; and
      (ii) a first recess defined by the lip wall and the outer neck surface;
   (c) an anchoring bowl comprising:
      (i) a bowl collar disposed around the circumference of the cylindrical neck body, the bowl collar comprising:
         (A) a bowl collar inner rim disposed at the proximal end of the cylindrical neck body; and
         (B) a bowl collar outer rim disposed radially external to the circumference of the cylindrical neck body and distal of the proximal end of the cylindrical neck body; and
      (ii) a bowl wall disposed around a circumference of the bowl collar, the bowl wall comprising:
         (A) a bowl wall inner rim disposed at the outer rim of the bowl collar; and
         (B) a bowl wall outer rim disposed radially external to the circumference of the bowl collar and proximal of the outer rim of the bowl collar; and
   wherein the deployable valve frame is expandable from an undeployed configuration to a deployed configuration, and wherein the outer neck surface of the cylindrical neck body is configured to be placed in contact with an inner wall of a valve annulus; and
   wherein the proximal end of the cylindrical neck body is configured to be disposed disposed in a first cavity and the distal end of the cylindrical neck body is configured to be disposed disposed in a second cavity.

2. The deployable valve frame of claim 1 wherein the deployable valve frame comprises a shape memory material that, when expanded to the deployed configuration within a target area, enhances frictional coupling of at least one of the anchoring lip and the anchoring bowl to the target area.

3. The deployable valve frame of claim 2 wherein expanding the deployable valve frame to the deployed configuration within a valve annulus enhances frictional coupling of the anchoring bowl to an inner surface of a first cavity and enhances frictional coupling of the anchoring lip to an inner surface of a second cavity.

4. The deployable valve frame of claim 1 wherein the bowl wall forms a convexly-shaped anchoring bowl.

5. The deployable valve frame of claim 1 wherein the anchoring lip comprises a lip and at least one prong extending radially from the lip.

6. The deployable valve frame of claim 1 wherein the anchoring lip comprises a lip and at least two prongs extending radially from the lip, wherein the at least two prongs are disposed around a circumference of the lip.

7. The deployable valve frame of claim 6 wherein the at least two prongs are spaced symmetrically around a circumference of the anchoring lip in relation to each other.

8. The deployable valve frame of claim 6 wherein the anchoring lip has a width ranging from 1 mm to 5 mm, and wherein each of the at least two prongs extends radially from the neck a distance ranging from 5 mm to 15 mm.

9. The deployable valve frame of claim 1 wherein the anchoring lip comprises a lip and three prongs extending radially from the lip, wherein each of the three prongs is disposed approximately 120 degrees around a circumference of the lip from the other two of the three prongs.

10. The deployable valve frame of claim 1 wherein the anchoring lip comprises a lip and four prongs extending radially from the lip, wherein the four prongs are disposed around the circumference of the lip to facilitate positioning of the four prongs under one or more native mitral valve leaflets.

11. A deployable valve frame comprising:
(a) a neck comprising:
  (i) a cylindrical neck body comprising an outer neck surface parallel to a longitudinal axis of the cylindrical neck body along an entire length of the elongate outer neck surface; and
  (ii) a lumen defined through the cylindrical neck body, wherein the lumen is sized and shaped to receive an implantable artificial valve;
(b) an anchoring lip disposed at a distal end of the cylindrical neck body, the anchoring lip comprising a lip wall disposed around a circumference of the cylindrical neck body which is configured to be placed within a second cavity, the lip wall comprising a lip wall outer rim disposed radially external to the circumference of the cylindrical neck body and proximal of the distal end of the cylindrical neck body; and
(c) an anchoring bowl disposed at a proximal end of the cylindrical neck body which is configured to be placed within a first cavity, the anchoring bowl comprising a bowl wall disposed around the circumference of the cylindrical neck body, the bowl wall comprising a bowl wall outer rim disposed radially external to the circumference of the cylindrical neck body,
wherein the deployable valve frame is expandable from an undeployed configuration to a deployed configuration wherein, in the deployed configuration, the outer neck surface of the cylindrical neck body is configured to be disposed within a valve annulus and placed in contact with an inner wall of the valve annulus.

12. The deployable valve frame of claim 11, wherein the anchoring lip further comprises a lip and at least one prong extending radially from the lip.

13. The deployable valve frame of claim 11, wherein the anchoring lip further comprises a lip and at least two prongs extending radially from the lip, wherein the at least two prongs are spaced symmetrically around a circumference of the anchoring lip in relation to each other.

14. The deployable valve frame of claim 11, wherein the anchoring lip further comprises a lip and three prongs extending radially from the lip, wherein each of the three prongs is disposed approximately 120 degrees around the circumference of the lip from the other two of the three prongs.

15. The deployable valve frame of claim 11, wherein the anchoring bowl is a convexly-shaped anchoring bowl further comprising:
(a) a bowl collar disposed around a circumference of the cylindrical neck body, the bowl collar comprising:
  (i) a bowl collar inner rim disposed at the proximal end of the cylindrical neck body; and
  (ii) a bowl collar outer rim disposed radially external to the circumference of the cylindrical neck body and distal of the proximal end of the cylindrical neck body; and
wherein the bowl wall is disposed around a circumference of the bowl collar, the bowl wall further comprising a bowl wall inner rim disposed at the bowl collar outer rim, and wherein the bowl wall outer rim is disposed radially external to the circumference of the bowl collar and proximal of the bowl collar outer rim.

16. The deployable valve frame of claim 11, wherein the anchoring bowl is a concavely-shaped anchoring bowl, wherein the bowl wall further comprises a bowl wall inner rim disposed at the proximal end of the cylindrical neck body, and wherein the bowl wall outer rim is disposed distal of the proximal end of the cylindrical neck body.

17. A deployable valve frame comprising:
(a) a neck configured to reach between a first cavity and a second cavity, the neck comprising:
  (i) a cylindrical neck body comprising an outer neck surface, an inner neck surface, a distal opening at a distal end, and a proximal opening at a proximal end; and
  (ii) a lumen defined through the cylindrical neck body by the inner neck surface, wherein the lumen is in fluidic communication with the distal opening and the proximal opening, wherein the lumen is sized and shaped to receive an implantable artificial valve;
(b) an anchoring lip comprising:
  (i) a lip wall disposed around a circumference of the cylindrical neck body, the lip wall comprising:
    (A) a lip wall inner rim disposed at the distal end of the cylindrical neck body; and
    (B) a lip wall outer rim disposed radially external to the circumference of the cylindrical neck body and proximal of the distal end of the cylindrical neck body; and
  (ii) a first recess defined by the lip wall and the outer neck surface;
(c) a concavely-shaped anchoring bowl comprising a bowl wall disposed around a circumference of the cylindrical neck body, the bowl wall comprising:
  (i) a bowl wall inner rim disposed at the proximal end of the cylindrical neck body; and (ii) a bowl wall outer rim disposed radially external to the circumference of the cylindrical neck body and distal of the proximal end of the cylindrical neck body; and wherein the deployable valve frame is expandable from an undeployed configuration to a deployed configuration, and wherein the outer neck surface of the cylindrical neck body is configured to be placed in contact with an inner wall of a valve annulus.

18. The deployable valve frame of claim 17 wherein the anchoring bowl further comprises a bowl lip extending radially from the bowl wall outer rim.

19. The deployable valve frame of claim 17 wherein the outer neck surface comprises an elliptical shape configured to conform with a shape of a native mitral valve annulus.

20. A deployable valve frame comprising:
(a) a neck comprising a cylindrical neck body having a proximal end configured to be disposed in a first cavity and a distal end configured to be disposed in a second cavity, and a lumen defined therethrough, the lumen configured to receive an implantable artificial valve;
(b) a bowl-shaped anchor coupled to the proximal end of the cylindrical neck body, wherein the bowl-shaped anchor is convexly shaped or concavely shaped; and
(c) a lip anchor coupled to the distal end of the cylindrical neck body, wherein the lip anchor comprises a lip wall disposed around a circumference of the cylindrical neck body, the lip wall comprising:
(i) a lip wall inner rim disposed at the distal end of the cylindrical neck body; and
(ii) a lip wall outer rim disposed radially external to the circumference of the cylindrical neck body and proximal of the distal end of the cylindrical neck body, wherein the lip wall outer rim comprises at least two prongs extending radially outwardly from the cylindrical neck body and extending proximally from the lip wall inner rim; and wherein the deployable valve frame is expandable from an undeployed configuration to a deployed configuration, and wherein an outer neck surface of the cylindrical neck body is configured to be placed in contact with an inner wall of a valve annulus.

21. The deployable valve frame of claim 20 wherein the lip anchor has a width ranging from 1 mm to 5 mm, wherein each of the at least two prongs extends radially from the neck a distance ranging from 5 mm to 15 mm.

\* \* \* \* \*